(12) United States Patent
Allan et al.

(10) Patent No.: US 9,708,402 B2
(45) Date of Patent: *Jul. 18, 2017

(54) ANTI-BAFF-ANTI-IL-17 BISPECIFIC ANTIBODIES

(71) Applicant: Eli Lilly and Company, Indianapolis, IN (US)

(72) Inventors: Barrett Allan, Encinitas, CA (US); Robert Jan Benschop, Indianapolis, IN (US); Jirong Lu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,782

(22) Filed: May 18, 2016

(65) Prior Publication Data

US 2016/0251430 A1    Sep. 1, 2016

Related U.S. Application Data

(63) Continuation of application No. 13/863,544, filed on Apr. 16, 2013, now Pat. No. 9,359,448.

(60) Provisional application No. 61/768,747, filed on Feb. 25, 2013, provisional application No. 61/636,302, filed on Apr. 20, 2012.

(51) Int. Cl.

| | |
|---|---|
| *C07K 16/00* | (2006.01) |
| *C12P 21/08* | (2006.01) |
| *A61K 39/395* | (2006.01) |
| *A61K 39/40* | (2006.01) |
| *C07K 16/24* | (2006.01) |
| *C07K 16/46* | (2006.01) |
| *C07K 16/28* | (2006.01) |
| *C07K 1/00* | (2006.01) |

(52) U.S. Cl.
CPC .......... *C07K 16/244* (2013.01); *C07K 16/241* (2013.01); *C07K 16/2875* (2013.01); *C07K 16/468* (2013.01); *C07K 2317/21* (2013.01); *C07K 2317/24* (2013.01); *C07K 2317/31* (2013.01); *C07K 2317/565* (2013.01); *C07K 2317/624* (2013.01); *C07K 2317/64* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS 9,359,448 B2 *  6/2016  Allan ................... C07K 16/468

OTHER PUBLICATIONS

Wu et al. Nature Biotechnology 25;1 1:1290-1297.*
Munshi et al. Clinical Cancer Research 2013, 19;13:3337-3344.*
Agnes Doreau, et al, "Interleukin 17 acts in synergy with B cell-activating factor to influence B cell biology and the pathophysiology of systemic lupus erythematosus", Nature Immunology, 2009, pp. 778-785, vol. 10 (7).
International Search Report.

* cited by examiner

*Primary Examiner* — Chun Dahle
(74) *Attorney, Agent, or Firm* — Megan N. Thobe; Gregory A. Cox

(57) ABSTRACT

Bispecific antibodies are provided that specifically bind B-cell Activating Factor of the TNF Family (BAFF) and Interleukin-17A (IL-17) and are characterized as having high affinity and strong neutralizing properties to both BAFF and IL-17. The bispecific antibodies of the invention are expected to be useful in treating Lupus Nephritis (LN), Systemic Lupus Erythematosus (SLE), Rheumatoid Arthritis (RA), Psoriasis (Ps), Ankylosing Spondylitis (AS), Psoriatic Arthritis (PA), primary Sjögren's Syndrome (pSS), or Multiple Myeloma (MM).

6 Claims, No Drawings

SEQUENCE LISTING

```
<160> NUMBER OF SEQ ID NOS: 4

<210> SEQ ID NO 1
<211> LENGTH: 714
<212> TYPE: PRT
<213> ORGANISM: Artificial Sequence
<220> FEATURE:
<223> OTHER INFORMATION: synthetic construct

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ile Leu Thr Gly Tyr Tyr Tyr Tyr Phe Asp Tyr
            100                 105                 110

Trp Gly Gln Gly Thr Leu Val Thr Val Ser Ser Ala Ser Thr Lys Gly
        115                 120                 125
```

```
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
    435                 440                 445

Gly Gly Gly Gly Ser Gly Gly Gly Thr Gly Gly Gly Ser Gln
450                 455                 460

Val Gln Leu Val Gln Ser Gly Ala Glu Val Lys Lys Pro Gly Ser Ser
465                 470                 475                 480

Val Lys Val Ser Cys Lys Ala Ser Gly Tyr Lys Phe Thr Asp Tyr His
                485                 490                 495

Ile His Trp Val Arg Gln Ala Pro Gly Gln Cys Leu Glu Trp Met Gly
            500                 505                 510

Val Ile Asn Pro Thr Tyr Gly Thr Thr Asp Tyr Asn Gln Arg Phe Lys
    515                 520                 525

Gly Arg Val Thr Ile Thr Ala Asp Glu Ser Thr Ser Thr Ala Tyr Met
530                 535                 540
```

```
Glu Leu Ser Ser Leu Arg Ser Glu Asp Thr Ala Val Tyr Tyr Cys Ala
545                 550                 555                 560

Arg Tyr Asp Tyr Phe Thr Gly Thr Gly Val Tyr Trp Gly Gln Gly Thr
                565                 570                 575

Leu Val Thr Val Ser Ser Gly Gly Gly Ser Gly Gly Gly Gly Ser
                580                 585                 590

Gly Gly Gly Gly Ser Gly Gly Gly Ser Asp Ile Val Met Thr Gln
            595                 600                 605

Thr Pro Leu Ser Leu Ser Val Thr Pro Gly Gln Pro Ala Ser Ile Ser
        610                 615                 620

Cys Arg Ser Ser Arg Ser Leu Val His Ser Arg Gly Glu Thr Tyr Leu
625                 630                 635                 640

His Trp Tyr Leu Gln Lys Pro Gly Gln Ser Pro Gln Leu Leu Ile Tyr
                645                 650                 655

Lys Val Ser Asn Arg Phe Ile Gly Val Pro Asp Arg Phe Ser Gly Ser
                660                 665                 670

Gly Ser Gly Thr Asp Phe Thr Leu Lys Ile Ser Arg Val Glu Ala Glu
            675                 680                 685

Asp Val Gly Val Tyr Tyr Cys Ser Gln Ser Thr His Leu Pro Phe Thr
690                 695                 700

Phe Gly Cys Gly Thr Lys Leu Glu Ile Lys
705                 710

<210> SEQ ID NO 2
<211> LENGTH: 214
<212> TYPE: PRT
<213> ORGANISM: Artificial Sequence
<220> FEATURE:
<223> OTHER INFORMATION: synthetic construct

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 2142
<212> TYPE: DNA
<213> ORGANISM: Artificial Sequence
<220> FEATURE:
<223> OTHER INFORMATION: synthetic construct

<400> SEQUENCE: 3
caggtgcaac tacagcagtg gggcgcagga ctgttgaagc cttcggagac cctgtccctc     60
acctgcgctg tctatggtgg gtccttcagt ggttactact ggagctggat tcgccagccc    120
ccagggaagg ggctggagtg gattgggaa atcaatcata gtggaagcac caactacaac    180
ccgtccctca gagtcgagt caccatatca gtagacacgt ccaagaacca gttctccctg    240
aaactgagct ctgtgaccgc cgcggacacg gctgtgtatt actgtgcgag agggtattac    300
gatattttga ctggttatta ttactacttt gactactggg gccagggaac cctggtcacc    360
gtctcctcag cctccaccaa gggcccatcg gtcttcccgc tagcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acgaagacct acacctgcaa cgtagatcac aagcccagca acaccaaggt ggacaagaga    660
gttgagtcca aatatggtcc cccatgccca ccctgcccag cacctgagtt cctggggggga    720 ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag ggcagccccg agagccacag gtgtacaccc tgcccccatc ccaggaggag   1080
atgaccaaga accaggtcag cctgacctgc ctggtcaaag gcttctaccc cagcgacatc   1140
gccgtggagt gggaaagcaa tgggcagccg gagaacaact acaagaccac gcctcccgtg   1200
ctggactccg acggctcctt cttcctctac agcaggctaa ccgtggacaa gagcaggtgg   1260
caggagggga atgtcttctc atgctccgtg atgcatgagg ctctgcacaa ccactacaca   1320
cagaagagcc tctccctgtc tcctgggagc ggaggatccg gggagggggg taccggagga   1380
gggggctcgc aggtgcagct ggtgcagtct ggggctgagg tgaagaagcc tgggtcctca   1440
gtgaaggttt cctgcaaggc atctggttac aagttcactg actaccatat tcattgggtg   1500
cgacaggccc ctggacaatg ccttgagtgg atgggagtaa ttaatcctac ttatggtact   1560
actgactaca atcagcggtt caaaggccgt gtcaccatta ccgcggacga atccacgagc   1620
acagcctaca tggagctgag cagcctgaga tctgaggaca cggccgtgta ttactgtgcg   1680
agatatgatt actttactgg gacgggtgtg tactggggcc aaggaaccct ggtcaccgtc   1740
tcctcaggtg gcggaggatc tggtggaggt ggctcaggag gtggcggaag cggcggaggt   1800
ggaagtgata ttgtgatgac tcagactcca ctctccctgt ccgtcacccc tggacagccg   1860
gcctccatct cctgcagatc tagtaggagc cttgtacaca gtcgtggaga aacctattta   1920
```

-continued

```
cattggtatc tgcagaagcc aggccaatct ccacagctcc taatttataa agtttccaac    1980
cggtttattg gggtcccaga cagattcagc ggcagtgggt caggcacaga tttcacactg    2040
aaaatcagca gggtggaggc cgaagatgtt ggggtttatt actgctctca aagtacacat    2100
cttccattca cgtttggctg cgggaccaag ctggagatca aa                      2142

<210> SEQ ID NO 4
<211> LENGTH: 642
<212> TYPE: DNA
<213> ORGANISM: Artificial Sequence
<220> FEATURE:
<223> OTHER INFORMATION: synthetic construct

<400> SEQUENCE: 4
gaaattgtgt tgacgcagtc tccagccacc ctgtctttgt ctccagggga aagagccacc     60
ctctcctgca gggccagtca gagtgttagc cgctacttag cctggtacca gcagaaacct    120
ggccaggctc ccaggctcct catctatgat gcatccaaca gggccactgg catcccagcc    180
aggttcagtg gcagtgggtc tgggacagac tccactctca ccatcagcag cctagagcct    240
gaagattttg cagtttatta ctgtcagcag cgtagcaact ggcctcggac gttcggccaa    300
gggaccaagg tggaaatcaa acgaactgtg gcggcgccat ctgtcttcat cttcccgcca    360
tctgatgagc agttgaaatc cggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcaa caccctgacg    540
ctgagcaaag cagactacga gaaacacaaa gtctacgcct gcgaagtcac ccatcagggc    600
ctgagctcgc ccgtcacaaa gagcttcaac aggggagagt gc                      642
```

ANTI-BAFF-ANTI-IL-17 BISPECIFIC ANTIBODIES

The present invention is in the field of medicine, particularly in the novel field of bispecific antibodies directed against B-cell Activating Factor of the TNF Family (BAFF) and Interleukin-17A (IL-17). The bispecific antibodies of the present invention are expected to be useful in treating Lupus Nephritis (LN), Systemic Lupus Erythematosus (SLE), Rheumatoid Arthritis (RA), Psoriasis (Ps), Ankylosing Spondylitis (AS). Psoriatic Arthritis (PA), primary Sjögren's Syndrome (pSS), or Multiple Myeloma (MM).

Increased levels of IL-17 have been associated with several conditions, diseases or disorders including airway inflammation, rheumatoid arthritis, osteoarthritis, bone erosion, intraperitoneal abscesses and adhesions, inflammatory bowel disorder, allograft rejection, psoriasis, certain types of cancer, angiogenesis, atherosclerosis and multiple sclerosis. IL-17 and IL-17 receptor are up regulated in the synovial tissue of rheumatoid arthritis patients. Blocking an IL-17 bioactivity reduces inflammation and bone erosion in various animal arthritis models. Furthermore, IL-17 has IL-1β independent effects on collagen matrix breakdown and inflammation and joint damage, while IL-17 has synergy with TNF-α to amplify inflammation. Thus, given its localized distribution at the site of inflammation, IL-17 appears to be a possible target for the treatment of rheumatoid arthritis and other inflammatory or autoimmune diseases with a potentially greater safety profile than drugs that target the systemic circulation of proinflammatory cytokines such as TNF-α.

The involvement of B-cell activating factor (BAFF) in the pathogenesis of autoimmune diseases is illustrated by BAFF overexpression in mice models, which leads to autoimmune disease mimicking rheumatoid arthritis, systemic lupus erythematosus and primary Sjögren's syndrome, as well as a twofold increase in occurrence of B cell lymphoma. In humans, numerous reports have shown elevated serum BAFF levels in SLE. RA, pSS, and systemic sclerosis patients. It has been demonstrated that BAFF promotes the expansion of Th17 cells and IL-17 is a crucial effector cytokine for BAFF-mediated proinflammatory effects during collagen-induced arthritis development. IL-17 has also been shown to act in synergy with BAFF to influence B cell biology and the pathophysiology of SLE. There is also evidence that both BAFF and IL-17 play a role in pathology associated with LN, in fact it has been reported that patients with LN have elevated levels of IL-17 and BAFF.

SLE is a highly heterogeneous and multisystem autoimmune disease that is characterized by the development of auto-antibodies and the formation of immune complexes. An estimated 30-60% of patients with SLE have renal involvement at some stage during the course of their disease. LN is a complex, multi-factorial autoimmune disease. If left untreated, the 5-year survival rate of patients with LN is 0-20%. The introduction of immunosuppressive therapy has greatly improved this situation and the current 10-year survival rate is 88%. However, this improvement comes at a cost for the patient, as many of these treatments have severe adverse events, especially since they have to be taken chronically. In addition, response is slow and often incomplete, with only 25-50% of patients reaching remission.

Co-administration of a BAFF antibody and IL-17 antibody requires either injections of two separate products or a single injection of a co-formulation of two different antibodies. Two injections would permit flexibility of dose amount and timing, but are inconvenient to patients both for compliance and pain. A co-formulation might also provide some flexibility of dose amounts, but it is often quite challenging or impossible to find formulation conditions that permit chemical and physical stability of both antibodies due to different molecular characteristics of the two different antibodies.

WO 199509917 discloses a method for producing bispecific, tetravalent antibodies (MAb-scFV) using recombinant DNA technology by producing a single chain fragment variable antibody fused to a complete antibody having a different specificity. This gene fusion is expressed by transfection resulting in a tetravalent antibody having dual specificity. WO2003016468 discloses anti-BAFF antibodies that bind and neutralize both soluble and membrane bound forms of human BAFF. WO2007070750 discloses anti-IL-17 antibodies that bind and neutralize human IL-17. However, when following the teachings in WO 199509917 to create a starting bispecific antibody comprising the anti-BAFF antibodies of WO2003016468 and the anti-IL-17 antibodies of WO2007070750, the present inventors discovered significant problems associated with chemical and physical stability. Many amino acid changes were required in the starting bispecific antibody to sufficiently overcome these problems. Neither the need for nor the actual changes are suggested in the art. Further, the several changes are not routine or derived from common general knowledge. Likewise, the single antibodies themselves did not have these problems, suggesting that the local environment around these areas differed in the context of bispecific antibodies. Thus, pharmacological intervention with a bispecific antibody that neutralizes both BAFF and IL-17 is needed.

The present invention provides a bispecific antibody comprising two first polypeptides and two second polypeptides.

The present invention also provides a DNA molecule comprising a polynucleotide sequence encoding the first polypeptide.

The present invention also provides a DNA molecule comprising a polynucleotide sequence encoding the second polypeptide.

The present invention also provides a DNA molecule comprising a polynucleotide sequence encoding the first polypeptide and the second polypeptide.

The present invention also provides a mammalian cell transformed with DNA molecule(s) which cell is capable of expressing a bispecific antibody comprising the first polypeptide and the second polypeptide.

The present invention also provides a process for producing a bispecific antibody comprising the first polypeptide and the second polypeptide, comprising cultivating the mammalian cell under conditions such that the bispecific antibody is expressed.

The present invention also provides a bispecific antibody produced by said process.

The present invention also provides a method of treating Systemic Lupus Erythematosus, Lupus Nephritis, Rheumatoid Arthritis, Psoriasis, Ankylosing Spondylitis, Psoriatic Arthritis, primary Sjögren's syndrome, or Multiple Myeloma comprising administering to a patient in need thereof an effective amount of a bispecific antibody.

The present invention also provides a bispecific antibody for use in therapy.

The present invention also provides a bispecific antibody for use in the treatment of Systemic Lupus Erythematosus, Lupus Nephritis, Rheumatoid Arthritis, Psoriasis, Ankylosing Spondylitis, Psoriatic Arthritis, primary Sjögren's syndrome, or Multiple Myeloma.

The present invention also provides a pharmaceutical composition comprising the bispecific antibody and one or more pharmaceutically acceptable carriers, diluents or excipients.

Human IL-17 is understood to mean a homodimeric protein comprising two human IL-17A proteins. A human IL-17A/F heterodimer is a human IL-17A protein and a human IL-17F protein.

A bispecific antibody is understood to mean an immunoglobulin molecule comprising four antigen binding sites, which binds two different antigens with specificity for each antigen in the MAb-scFV format. The bispecific antibody is capable of binding each antigen alone or each antigen simultaneously.

The bispecific antibody of the present invention comprises two first polypeptides and two second polypeptides. Each of the first polypeptides forms an inter-chain disulfide bond with each of the second polypeptides, and the first polypeptide forms two inter-chain disulfide bonds with the other first polypeptide, and each of the first polypeptides forms several intra-chain disulfide bonds. The relationship of the polypeptides and the disulfide bonds are shown in the following schematic:

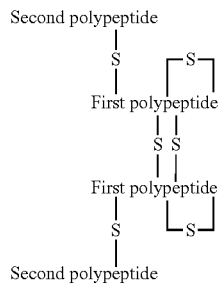

The amino acid sequence of the first polypeptide is:

(SEQ ID NO: 1)

```
QVQLOQWGAG LLKPSETLSL TCAVYGGSFS GYYWSWIRQP PGKGLEWIGE   50
INHSGSTNYN PSLKSRVTIS VDTSKNQFSL KLSSVTAADT AVYYCARGYY  100
DILTGYYYYF DYWGQGTLVT VSSASTKGPS VFPLAPCSRS TSESTAALGC  150
LVKDYFPEPV TVSWNSGALT SGVHTFPAVL QSSGLYSLSS VVTVPSSSLG  200
TKTYTCNVDH KPSNTKVDKR VESKYGPPCP PCPAPEFLGG PSVFLFPPKP  250
KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ  350
VYTLPPSQEE MTKNQVSLTC LVKGFYPSDI AVEWESNGQP ENNYKTTPPV  400
LDSDGSFFLY SRLTVDKSRW QEGNVFSCSV MHEALHNHYT QKSLSLSPGG  450
GGSGGGGTGG GGSQVQLVQS GAEVKKPGSS VKVSCKASGY KFTDYHIHWV  500
RQAPGQCLEW MGVINPTYGT TDYNQRFKGR VTITADESTS TAYMELSSLR  550
SEDTAVYYCA RYDYFTGTGV YWGQGTLVTV SSGGGGSGGG GSGGGGSGGG  600
GSDIVMTQTP LSLSVTPGQP ASISCRSSRS LVHSRGETYL HWYLQKPGQS  650
PQLLIYKVSN RFIGVPDRFS GSGSGTDFTL KISRVEAEDV GVYYCSQSTH  700
LPFTEGCGTK LEIK.                                        714
```

The amino acid sequence of the second polypeptide is:

(SEQ ID NO: 2)

```
EIVLTQSPAT LSLSPGERAT LSCRASQSVS RYLAWYQQKP GQAPRLLIYD   50
ASNRATGIPA RFSGSGSGTD STLTISSLEP EDFAVYYCQQ RSNWPRTFGQ  100
GTKVEIKRTV AAPSVFIFPP SDEQLKSGTA SVVCLLNNFY PREAKVQWKV  150
DNALQSGNSQ ESVTEQDSKD STYSLSNTLT LSKADYEKHK VYACEVTHQG  200
LSSPVTKSFN RGEC.                                        214
```

The inter-chain disulfide bond of each of the first polypeptides and each of the second polypeptides forms between cysteine residue 137 of SEQ ID NO:1 and cysteine residue 214 of SEQ ID NO:2. The first polypeptide forms two inter-chain disulfide bonds with the other first polypeptide. The first inter-chain disulfide bond forms between cysteine residue 229 of the first polypeptide of SEQ ID NO: 1 and cysteine residue 229 of the other first polypeptide of SEQ ID NO: 1. The second inter-chain disulfide bond forms between cysteine residue 232 of the first polypeptide of SEQ ID NO: 1 and cysteine residue 232 of the other first polypeptide of SEQ ID NO: 1.

Within the scFV, an engineered intra-chain disulfide bond is formed between cysteine residue 507 of SEQ ID NO: 1 and cysteine residue 707 of SEQ ID NO:1. Also, an intra-chain disulfide bond is formed between cysteine residue 625 of SEQ ID NO:1 and cysteine residue 695 of SEQ ID NO:1. Within the MAb, intra-chain disulfide bonds that normally occur in an IgG4 antibody are formed between cysteine residue 22 of SEQ ID NO: 1 and cysteine residue 95 of SEQ ID NO: 1, between cysteine residue 150 of SEQ ID NO:1 and cysteine residue 206 of SEQ ID NO: 1, between cysteine residue 264 of SEQ ID NO:1 and cysteine residue 324 of SEQ ID NO:1, between cysteine residue 370 of SEQ ID NO:1 and cysteine residue 428 of SEQ ID NO:1, between cysteine residue 485 of SEQ ID NO:1 and cysteine residue 559 of SEQ ID NO:1, between cysteine residue 23 of SEQ ID NO:2 and cysteine residue 88 of SEQ ID NO:2, and between cysteine residue 134 of SEQ ID NO:2 and cysteine residue 194 of SEQ ID NO:2.

The first polypeptide comprises a first heavy chain variable region (HCVR1), a heavy chain constant region (CH), a second heavy chain variable region (HCVR2) and a second light chain variable region (LCVR2). The second polypeptides comprises a first light chain variable region (LCVR1) and a light chain constant region (CL). The HCVR and LCVR regions can be further subdivided into regions of hypervariability, termed complementarity determining regions (CDR), interspersed with framework regions (FR). Each HCVR and LCVR is composed of three CDRs and four FRs, arranged from amino-terminus to carboxyl-terminus in the following order: FR1, CDR1, FR2, CDR2, FR3, CDR3, FR4.

The 3 CDRs of HCVR1 are referred to as CDRH1-1, CDRH1-2, and CDRH1-3 and the 3 CDRs of HCVR2 are referred to as CDRH2-1, CDRH2-2, and CDRH2-3 and the 3 CDRs of LCVR1 are referred to as CDRL1-1, CDRL1-2 and CDRL1-3 and the 3 CDRs of LCVR2 are referred to as CDRL2-1, CDRL2-2 and CDRL2-3.

The CH is fused to HCVR2 by an amino acid linker (L1). HCVR2 is fused to LCVR2 by an amino acid linker (L2).

The relationship of the various regions and linkers is as follows:

| | Region | Positions |
|---|---|---|
| Polypeplide 1 - SEQ ID NO: 1 | | |
| HCVR1 | FRH1-1 | 1-26 |
| BAFF | CDRH1-1 | 27-35 |
| | FRH1-2 | 36-49 |
| | CDRH1-2 | 50-65 |
| | FRH1-3 | 66-97 |
| | CDRH1-3 | 98-112 |
| | FRH1-4 | 113-123 |
| Constant | CH | 124-447 |
| Linker | L1 | 448-463 |
| HCVR2 | FRH2-1 | 464-487 |
| IL-17 | CDRH2-1 | 488-498 |
| | FRH2-2 | 499-512 |
| | CDRH2-2 | 513-528 |
| | FRH2-3 | 529-561 |
| | CDRH2-3 | 562-571 |
| | FRH2-4 | 572-582 |
| Linker | L2 | 583-602 |
| LCVR2 | FRL2-1 | 603-625 |
| IL-17 | CDRL2-1 | 626-641 |
| | FRL2-2 | 642-656 |
| | CDRL2-2 | 657-663 |
| | FRL2-3 | 664-695 |
| | CDRL2-3 | 696-704 |
| | FRL2-4 | 705-714 |
| Polypeplide 2 - SEQ ID NO: 2 | | |
| LCVR1 | FRL1-1 | 1-23 |
| BAFF | CDRL1-1 | 24-34 |
| | FRLI-2 | 35-49 |
| | CDRL1-2 | 50-56 |
| | FRL1-3 | 57-88 |
| | CDRL1-3 | 89-97 |
| | FRL1-4 | 98-107 |
| Constant | CL | 108-214 |

Bispecific Antibody Engineering

Significant problems associated with chemical and physical stability were encountered when constructing a bispecific antibody in the MAb-scFv format with the anti-IL-17 binding portion in the scFv configuration. Chemical modifications were made in the CDRL2-1 and CDRH2-2 portions of the bispecific antibody that improved physical stability and reduced concentration-dependent aggregation. Extensive protein stability and solubility studies identified chemically unstable residues in CDRL2-1 and CDRH2-2. These labile residues were replaced with charge neutral amino acids using targeted libraries constructed by codon depletion. Additionally, the electrostatic surface of the bispecific antibody was calculated and charged patches were identified. Disruptions of these charged patches in the scFv led to a decrease in protein self-association. However, a mutation was identified in the CDRH2-1 portion of the bispecific antibody that rebalanced the surface electrostatic distribution, and improved physical stability and solubility at high concentrations. None of the above issues were encountered in the parental single antibodies. These problems were encountered only in the context of constructing a bispecific antibody in the MAb-scFv format, suggesting that the local environment around the mutated areas of the single antibody differed in the context of a bispecific antibody.

Further chemical modifications were made to stabilize the HCVR2/LCVR2 interface in the IL-17 portion of the bispecific antibody, and to reduce bispecific antibody aggregation. Studies conducted to determine the aggregation showed that the observed protein self-association was not driven by conformational instability of the individual HCVR2 or LCVR2 domains, but rather by the opening or breathing of the HCVR2/LCVR2 interface, leading to intermolecular protein interactions. Thus, various intra-chain disulfide bonds were introduced into the HCVR2/LCVR2 interface of the IL-17 portion of the bispecific antibody. One such intra-chain disulfide bond occurs in each of the first polypeptides between cysteine residue 507 of SEQ ID NO: 1 and cysteine residue 707 of SEQ ID NO: 1. This disulfide bond covalently connects the HCVR2/LCVR2 interface in the IL-17 portion of the bispecific antibody, which stabilizes the HCVR2/LCVR2 interface and reduces intermolecular protein interactions that can lead to physical instability and unfavorable formulation limitations. Out of the nine different disulfide bonds tested, 8 of which expressed functional protein, the magnitude of affinity loss ranged from about 2 to about 35-fold. The intra-chain disulfide bond in each of the first polypeptides between cysteine residue 507 of SEQ ID NO: 1 and cysteine residue 707 of SEQ ID NO: 1 best stabilized the HCVR2/LCVR2 interface while maintaining optimal binding affinity for IL-17.

In addition, studies indicated that linker length for L1 affected binding kinetics. Kinetic analysis (by surface plasmon resonance) showed that a 10 amino acid linker caused a 2-fold slower $K_{on}$ rate compared to 15 amino acid and 20 amino acid linkers. Thus, a linker length of 15 was introduced into the bispecific antibody of the present invention.

Bispecific Antibody Binding

The bispecific antibodies of the present invention bind both human BAFF and human IL-17 and neutralize at least one human BAFF bioactivity and at least one human IL-17 bioactivity in vitro or in vivo. The bispecific antibodies of the present invention are potent inhibitors of IL-17 in the presence and absence of BAFF in vitro. The bispecific antibodies of the present invention are potent inhibitors of both soluble and membrane-bound BAFF in the presence or absence of IL-17 in vitro. The bispecific antibodies of the invention are further characterized as having a binding affinity ($K_D$) for human BAFF in the range of 150 pM to 1 pM and human IL-17 in the range of 50 pM to 1 pM. The bispecific antibodies have a binding affinity for human IL-17A/F heterodimer of about 90 pM.

The bispecific antibodies effectively neutralize soluble as well as membrane-bound BAFF and this neutralization is not affected by the presence of saturating amounts of human IL-17. The bispecific antibodies effectively neutralize human IL-17 and this neutralization is not affected by the presence of saturating amounts of human BAFF.

Bispecific Antibody Expression

Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. The first polypeptide and the second polypeptide may be expressed independently from different promoters to which they are operably linked in one vector or, alternatively, the first polypeptide and the second polypeptide may be expressed independently from different promoters to which they are operably linked in two vectors—one expressing the first polypeptide and one expressing the second polypeptide.

A host cell includes cells stably or transiently transfected, transformed, transduced or infected with one or more expression vectors expressing a first polypeptide, a second polypeptide or both a first polypeptide and a second polypeptide of the invention. Creation and isolation of host cell lines producing a bispecific antibody of the invention can be accomplished using standard techniques known in the art. Mammalian cells are preferred host cells for expression of bispecific antibodies. Particular mammalian cells are HEK 293, NS0, DG-44, and CHO. Preferably, the bispecific antibodies are secreted into the medium in which the host cells are cultured, from which the bispecific antibodies can be recovered or purified.

It is well known in the art that mammalian expression of antibodies results in glycosylation. Typically, glycosylation occurs in the Fc region of the antibody at a highly conserved N-glycosylation site. N-glycans typically attach to asparagine. Each of the first polypeptides is glycosylated at asparagine residue 300 of SEQ ID NO: 1.

A particular DNA polynucleotide sequence encoding the first polypeptide having an amino acid sequence of SEQ ID NO:1 is:

(SEQ ID NO: 3)
```
cAGGTGCAACTACAGCAGTGGGGCGCAGGACTGTTGAAGCCTTCGGAGAC
CCTGTCCCTCACCTGCGCTGTCTATGGTGGGTCCTTCAGTGGTTACTACT
GGAGCTGGATTCGCCAGCCCCCAGGGAAGGGGCTGGAGTGGATTGGGGAA
ATCAATCATAGTGGAAGCACCAACTACAACCCGTCCCTCAAGAGTCGAGT
CACCATATCAGTAGACACGTCCAAGAACCAGTTCTCCCTGAAACTGAGCT
CTGTGACCGCCGCGGACACGGCTGTGTATTACTGTGCGAGAGGGTATTAC
GATATTTTGACTGGTTATTATTACTACTTTGACTACTGGGGCCAGGGAAC
CCTGGTCACCGTCTCCTCAGCCTCCACCAAGGGCCCATCGGTCTTCCCGC
TAGCGCCCTGCTCCAGGAGCACCTCCGAGAGCACAGCCGCCCTGGGCTGC
CTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAG
GACTCTACTCCCTCAGCAGCGTGGTGACCGTGCCCTCCAGCAGCTTGGGC
ACGAAGACCTACACCTGCAACGTAGATCACAAGCCCAGCAACACCAAGGT
GGACAAGAGAGTTGAGTCCAAATATGGTCCCCCATGCCCACCCTGCCCAG
CACCTGAGTTCCTGGGGGGACCATCAGTCTTCCTGTTCCCCCCAAAACCC
AAGGACACTCTCATGATCTCCCGGACCCCTGAGGTCACGTGCGTGGTGGT
GGACGTGAGCCAGGAAGACCCCGAGGTCCAGTTCAACTGGTACGTGGATG
GCGTGGAGGTGCATAATGCCAAGACAAAGCCGCGGGAGGAGCAGTTCAAC
AGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCT
CCATCGAGAAAACCATCTCCAAAGCCAAAGGGCAGCCCCGAGAGCCACAG
GTGTACACCCTGCCCCCATCCCAGGAGGAGATGACCAAGAACCAGGTCAG
CCTGACCTGCCTGGTCAAAGGCTTCTACCCCAGCGACATCGCCGTGGAGT
GGGAAAGCAATGGGCAGCCGGAGAACAACTACAAGACCACGCCTCCCGTG
CTGGACTCCGACGGCTCCTTCTTCCTCTACAGCAGGCTAACCGTGGACAA
GAGCAGGTGGCAGGAGGGGAATGTCTTCTCATGCTCCGTGATGCATGAGG
CTCTGCACAACCACTACACACAGAAGAGCCTCTCCCTGTCTCCTGGAGGC
GGAGGATCCGGGGAGGGGGTACCGGAGGAGGGGCTCGCAGGTGCAGCT
GGTGCAGTCTGGGGCTGAGGTGAAGAAGCCTGGGTCCTCAGTGAAGGTTT
CCTGCAAGGCATCTGGTTACAAGTTCACTGACTACCATATTCATTGGGTG
CGACAGGCCCCTGGACAATGCCTTGAGTGGATGGGAGTAATTAATCCTAC
TTATGGTACTACTGACTACAATCAGCGGTTCAAAGGCCGTGTCACCATTA
CCGCGGACGAATCCACGAGCACAGCCTACATGGAGCTGAGCAGCCTGAGA
TCTGAGGACACGGCCGTGTATTACTGTGCGAGATATGATTACTTTACTGG
GACGGGTGTGTACTGGGGCCAAGGAACCCTGGTCACCGTCTCCTCAGGTG
GCGGAGGATCTGGTGGAGGTGGCTCAGGAGGTGGCGGAAGCGGCGGAGGT
```

-continued

```
GGAAGTGATATTGTGATGACTCAGACTCCACTCTCCCTGTCCGTCACCCC

TGGACAGCCGGCCTCCATCTCCTGCAGATCTAGTAGGAGCCTTGTACACA

GTCGTGGAGAAACCTATTTACATTGGTATCTGCAGAAGCCAGGCCAATCT

CCACAGCTCCTAATTTATAAAGTTTCCAACCGGTTTATTGGGGTCCCAGA

CAGATTCAGCGGCAGTGGGTCAGGCACAGATTTCACACTGAAAATCAGCA

GGGTGGAGGCCGAAGATGTTGGGGTTTATTACTGCTCTCAAAGTACACAT

CTTCCATTCACGTTGGCTGCGGGACCAAGCTGGAGATCAAA.
```

A particular DNA polynucleotide sequence encoding the second polypeptide having an amino acid sequence of SEQ ID NO:2 is:

```
                                            (SEQ ID NO: 4)
GAAATTGTGTTGACGCAGTCTCCAGCCACCCTGTCTTTGTCTCCAGGGGA

AAGAGCCACCCTCTCCTGCAGGGCCAGTCAGAGTGTTAGCCGCTACTTAG

CCTGGTACCAGCAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTCCACTCTCACCATCAGCAGCCTAGAGCCTGAAGATTTTG

CAGTTTATTACTGTCAGCAGCGTAGCAACTGGCCTCGGACGTTCGGCCAA

GGGACCAAGGTGGAAATCAAACGAACTGTGGCGGCGCCATCTGTCTTCAT

CTTCCCGCCATCTGATGAGCAGTTGAAATCCGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAACACCCTGACGCTGAGCAAAG

CAGACTACGAGAAACACAAAGTCTACGCCTGCGAAGTCACCCATCAGGGC

CTGAGCTCGCCCCTCACAAAGAGCTTCAACAGGGGAGAGTGC.
```

Medium, into which a bispecific antibody has been secreted, may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

There may be a need to reduce the level of misfolded bispecific antibody present in the medium. Misfolded bispecific antibody is also known as diabody. Misfolding results when one or more disulfide bonds form incorrectly, either inter or intra chains. The misfolded bispecific antibody may be purified by conventional techniques. For example, the medium containing the misfolded bispecific antibody may be applied to and eluted from strong cation exchange resin. For example, SP-Sepharose HP strong cation exchange resin is used to purify correctly folded bispecific antibody from diabody. The pH of the medium containing the diabody is adjusted to pH 8 using 1M Tris Base. The medium is loaded onto an SP-Sepharose HP column, washed with 2 column volumes of 20 mM Tris, pH 8 and eluted with 20 mM Tris, 100 mM NaCl, pH8 over 30 column volumes (0-70 mM NaCl). The collected pools can be assessed for high molecular weight versus main peak. A typical result is an improvement from 10% diabody to 1% diabody with 71% recovery.

In another example, Poros HS 50 strong cation exchange resin is used to purify correctly folded bispecific antibody from diabody. The pH of the medium containing the diabody is adjusted to pH 8 using 1M Tris Base. The medium is loaded onto an SP-Sepharose HP column and eluted with 20 mM Tris, 100 mM NaCl, pH8 over 15 column volumes (15-50 mM NaCl). The collected pools can be assessed for high molecular weight versus main peak. A typical result is an improvement from 10% diabody to 1% diabody with 57% recovery.

Therapeutic Uses

A patient refers to a mammal, preferably a human with a disease, disorder or condition that would benefit from a decreased level of BAFF and/or IL-17 or decreased bioactivity of BAFF and/or IL-17.

Treatment and/or treating are intended to refer to all processes wherein there may be a slowing, interrupting, arresting, controlling, or stopping of the progression of the disorders described herein, but does not necessarily indicate a total elimination of all disorder symptoms. The bispecific antibody of the present invention is expected to treat systemic lupus erythematosus, lupus nephritis, rheumatoid arthritis, psoriasis, ankylosing spondylitis, psoriatic arthritis, primary Sjögren's syndrome or multiple myeloma.

Pharmaceutical Composition

A bispecific antibody of the invention can be incorporated into a pharmaceutical composition suitable for administration to a patient. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., *Remington, The Science and Practice of Pharmacy*, 19$^{th}$ Edition, Gennaro, Ed., Mack Publishing Co., Easton, Pa. 1995 which provides a compendium of formulation techniques as are generally known to practitioners. Suitable carriers for pharmaceutical compositions include any material which, when combined with a bispecific antibody of the invention, retains the molecule's activity and is non-reactive with the patient's immune system. A pharmaceutical composition of the present invention comprises a bispecific antibody and one or more pharmaceutically acceptable carriers, diluents or excipients.

A pharmaceutical composition comprising a bispecific antibody of the present invention can be administered to a patient at risk for or exhibiting diseases or disorders as described herein using standard administration techniques.

A pharmaceutical composition of the invention contains an effective amount of a bispecific antibody of the invention. An effective amount refers to an amount necessary (at dosages and for periods of time and for the means of administration) to achieve the desired therapeutic result. An effective amount of the bispecific antibody may vary according to factors such as the disease state, age, sex, and weight of the individual, and the ability of the antibody or antibody portion to elicit a desired response in the individual. An effective amount is also one in which any toxic or detrimental effect of the bispecific antibody, are outweighed by the therapeutically beneficial effects.

The bispecific antibody of the following example of expression and demonstration of properties comprises two first polypeptides having amino acid sequences of SEQ ID NO: 1 and two second polypeptides having amino acid sequences of SEQ ID NO:2 wherein each of the first polypeptides forms an inter-chain disulfide bond with each of the second polypeptides between cysteine residue 137 of SEQ ID NO:1 and cysteine residue 214 of SEQ ID NO:2, and the first polypeptide forms two inter-chain disulfide bonds with the other first polypeptide between cysteine residue 229 first polypeptide of SEQ ID NO:1 and cysteine residue 229 of the other first polypeptide of SEQ ID NO:1 and between cysteine residue 232 first polypeptide of SEQ ID NO:1 and cysteine residue 232 of the other first polypeptide of SEQ ID NO: 1, and each of the first polypeptides forms an intra-chain disulfide bond between cysteine residue 22 and cysteine residue 95 of SEQ ID NO:1, between cysteine residue 150 of SEQ ID NO:1 and cysteine residue 206 of SEQ ID NO:1, between cysteine residue 264 of SEQ ID NO:1 and cysteine residue 324 of SEQ ID NO:1, between cysteine residue 370 of SEQ ID NO: 1 and cysteine residue 428 of SEQ ID NO: 1, between cysteine residue 485 of SEQ ID NO: 1 and cysteine residue 559 of SEQ ID NO: 1, between cysteine residue 507 of SEQ ID NO: 1 and cysteine residue 707 of SEQ ID NO: 1, and between cysteine residue 625 of SEQ ID NO:1 and cysteine residue 695 of SEQ ID NO:1, and each of the second polypeptides forms an intra-chain disulfide bond between cysteine residue 23 of SEQ ID NO:2 and cysteine residue 88 of SEQ ID NO:2, and between cysteine residue 134 of SEQ ID NO:2 and cysteine residue 194 of SEQ ID NO:2, and wherein each of the first polypeptides is glycosylated at asparagine residue 300 of SEQ ID NO:1. The ratio of correctly folded bispecific antibody to misfolded diabody is on the order to 90:10.

Expression of Bispecific Antibody

The bispecific antibody can be expressed and purified essentially as follows. A glutamine synthetase (GS) expression vector containing the DNA of SEQ ID NO:3 (encoding the first polypeptide having amino acid sequence of SEQ ID NO:1) and SEQ ID NO:4 (encoding the light chain amino acid sequence of SEQ ID NO:2) is used to transfect the Chinese hamster cell line, CHOK1SV (Lonza Biologics PLC, Slough, United Kingdom) by electroporation. The expression vector encodes an SV Early (Simian Virus 40E) promoter and the gene for GS. Expression of GS allows for the biochemical synthesis of glutamine, an amino acid required by the CHOK1SV cells. Post-transfection, cells undergo bulk selection with 50 μM L-methionine sulfoximine (MSX). The inhibition of GS by MSX is utilized to increase the stringency of selection. Cells with integration of the expression vector cDNA into transcriptionally active regions of the host cell genome can be selected against CHOK1SV wild type cells, which express an endogenous level of GS. Transfected pools are plated at low density to allow for close-to-clonal outgrowth of stable expressing cells. The masterwells are screened for bispecific antibody expression and then scaled up in serum-free, suspension cultures to be used for production. Clarified medium, into which the bispecific antibody has been secreted, is applied to a Protein A affinity column that has been equilibrated with a compatible buffer, such as phosphate buffered saline (pH 7.4). The column is washed to remove nonspecific binding components. The bound bispecific antibody is eluted, for example, by pH gradient (such as 0.1 M sodium phosphate buffer pH 6.8 to 0.1 M sodium citrate buffer pH 2.5). Bispecific antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. The bispecific antibody may be concentrated and/or sterile filtered using common techniques. The purity of the bispecific antibody after these chromatography steps is greater than 98%. The bispecific antibody may be immediately frozen at −70° C. or stored at 4° C. for several months.

Binding Affinity to IL-17 and BAFF

Binding affinity and binding stoichiometry of the bispecific antibody to human IL-17 and human BAFF is determined using a surface plasmon resonance assay on a Biacore 2000 instrument primed with HBS-EP+ (GE Healthcare, 10 mM Hepes pH7.4+150 mM NaCl+3 mM EDTA+0.05% surfactant P20) running buffer and analysis temperature set at 25° C. A CM5 chip containing immobilized protein A (generated using standard NHS-EDC amine coupling) on all four flow cells (Fc) is used to employ a capture methodology. Antibody samples are prepared at 10 mcg/mL by dilution into running buffer. Human IL-17 or human BAFF are prepared at final concentrations of 20.0, 10.0, 5.0, 2.5, 1.25 and 0 (blank) nM by dilution into running buffer. Each analysis cycle consists of (1) capturing antibody samples on separate flow cells (Fc2, Fc3, and Fc4), (2) injection of 250 mcL (300-sec) of human IL-17 or human BAFF over all Fc at 50 mcL/min, (3) return to buffer flow for 20 min to monitor dissociation phase, (4) regeneration of chip surfaces with a 5 mcL (30-sec) injection of glycine, pH1.5, (5) equilibration of chip surfaces with a 10 mcL (60-sec) injection of HBS-EP+. Data are processed using standard double-referencing and fit to a 1:1 binding model using Biacore 2000 Evaluation software, version 4.1, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) is calculated as from the relationship $K_D = k_{off}/k_{on}$, and is in molar units.

TABLE 1

Binding affinity to human IL-17 and human BAFF by the bispecific antibody.

| Antigen | $k_{on}$ Avg ± SD $M^{-1}s^{-1}$ ($10^6$) | $k_{off}$ Avg ± SD $s^{-1}$ | $K_D$ Avg ± SD pM | n |
|---|---|---|---|---|
| Human IL-17 | 2.5 ± 0.4 | 3.7 (±1.8) × $10^{-5}$ | 14 ± 5 | 3 |
| Human BAFF | 2.3 ± 0.9 | 1.2 (±0.5) × $10^{-4}$ | 60 ± 50 | 3 |

These results demonstrate that the bispecific antibody of the present invention binds human IL-17 and human BAFF.

Simultaneous Binding of IL-17 and BAFF

BIAcore 2000 instrument is used to determine whether human IL-17 and human BAFF can bind to the bispecific antibody simultaneously. Except as noted, all reagents and materials are purchased from BIAcore AB (Upsala, Sweden). All measurements are performed at 25° C. HBS-EP+ buffer (150 mM sodium chloride, 3 mM EDTA, 0.05% (w/v) surfactant P-20, and 10 mM HEPES, pH7.4) is used as the running buffer and sample buffer. Protein A is immobilized on flow cells 1 and 2 of a CM4 sensor chip using an amine coupling kit. The bispecific antibody is first captured on flow cell 2, followed by injection of human IL-17 at 20 nM for 5 min to saturate IL-17 binding site. After binding of IL-17, human BAFF at 20 nM is then injected for 5 min. and additional binding signal is observed. Chip surface is then regenerated using 10 mM Glycine pH 1.5. The same process is repeated except with a different order of human IL-17 and human BAFF. The stoichiometry is calculated to ensure complete saturation of human IL-17 or human BAFF to the bispecific antibody. The stoichiometry of human IL-17 to the bispecific antibody is typically at ~1.3 based on a kinetic binding experiment. Similarly, the stoichiometry of human BAFF to the bispecific antibody is typically at ~1.0 based on a kinetic binding experiment. Control BAFF Ab is 4A5-3.1.1-B4 of U.S. Pat. No. 7,317,089. Control IL-17 Ab is Fab 126 of U.S. Pat. No. 7,838,638.

TABLE 2

Simultaneous binding of human IL-17 and human BAFF to the bispecific antibody.

| Antibody | First analyte | Δ RU | Second analyte | Δ RU |
|---|---|---|---|---|
| Bispecific | BAFF | 22 | IL-17 | 11 |
| Bispecific | IL-17 | 15 | BAFF | 23 |
| IL-17 Ab | BAFF | 0 | IL-17 | 32 |
| IL-17 Ab | IL-17 | 16 | BAFF | 0 |
| BAFF Ab | BAFF | 33 | IL-17 | 0 |
| BAFF Ab | IL-17 | 0 | BAFF | 32 |

These results demonstrate that the bispecific antibody of the present invention can bind human IL-17 and human BAFF simultaneously as shown by the increase in response units (ΔRU) from the two ligands binding to the bispecific antibody.

Inhibition of IL-17 Induced CXCL1 Production In Vitro from HT-29 Cells

HT-29 cells are human colorectal adenocarcinoma epithelial cells that naturally express the IL-17 receptor. Incubation of HT29 cells with human IL-17 results in the production of CXCL1, which can be measured using a commercially available ELISA.

A dose range of the bispecific antibody from 41200 to 2.64 pM is evaluated (final concentration based on monomeric MW of bispecific antibody (=100 kDa)). Each test concentration of bispecific antibody is then added (50 mcl) to wells containing recombinant IL-17 (final IL-17 concentration in the well is 3.75 nM (based on monomeric MW of IL-17 (=16 kDa)). Testing is carried out in triplicate wells per treatment. Assay medium is used for "medium alone" and "IL-17 alone" controls. An IL-17 neutralizing antibody (Fab 126 of U.S. Pat. No. 7,838,638) is used as positive control in the assay. Plates containing IL-17 and antibody mixtures are incubated for 60 to 90 minutes at 37° C., 95% relative humidity, 5% CO2 in the inner wells of tissue-culture treated 96 well plates. In a variation of this assay, a saturating concentration of human BAFF is added (1.25 nM final concentration based on monomeric MW of BAFF (=20 kDa)), with the goal to determine if bispecific antibody would still be able to neutralize IL-17 when simultaneously bound to BAFF. HT-29 cells are routinely cultured in assay medium (McCoy's 5A containing 10% FBS, penicillinG (0.2 U/mL) and streptomycin (0.2 mcg/mL)). On the day of the assay, the cells are rinsed with HBSS and detached from the culture flasks with trypsin+ EDTA. The trypsin is inactivated with assay medium. HT-29 cells are then centrifuged at 500×g for 5 minutes at RT. The cell pellet is resuspended in assay medium. Cell density is measured with a hemocytometer, and 20,000 HT-29 cells (in 100 mcl) are added to the 96-well plates containing the antibody/IL-17 mixture. Two hundred mcl of PBS is added to each of the unused edge wells (without cells) to reduce edge effects resulting from evaporation. The 96-well plates are placed in a tissue culture incubator (37° C., 95% relative humidity, 5% CO2) for approximately 48 hours.

At the end of the assay, the plates are centrifuged (500×g for 5 minutes at RT), and the cell culture medium is transferred to polypropylene 96-well plates, which are sealed and frozen at −80° C. On the day of measuring CXCL1 by ELISA, the plates are thawed at RT. CXCL1 levels in medium (either undiluted, or diluted 1:3) are measured with a CXCL1 sandwich ELISA (R&D Systems DuoSet #DY275), as per the manufacturer's instructions, using the following buffers and modifications: 1×ELISA wash buffer from BioFX Labs (from 10×, #WSHW-1000-01); sample and standard volume of 50 mcL per well; substrate from BioFX Labs (1 component HRP substrate. #TMBW-1000-01); a stop solution from BioFX Labs (#LSTP-1000-01; 100 mcl per well). At the end of the ELISA reactions, plates were read at 450 nm on a microplate reader (Molecular Devices SpectraMax 190). Data are collected as % of maximum amount of CXCL1 produced (with IL-17 alone being 100%). The concentration where 50% of the IL-17-induced response is inhibited (IC50) by either bispecific antibody or the positive control is calculated using a 4 parameter sigmoidal fit of the data (GraphPad Prism).

The results demonstrate that the bispecific antibody of the present invention inhibited IL-17-induced secretion of CXCL1 by HT-29 cells in a concentration-dependent manner. The inhibition is comparable to that observed with the positive control antibody (with an IC50 for bispecific antibody of 2.00±0.21 nM versus 1.86±0.22 nM for the positive control antibody (average of 3 independent experiments±SEM)), whereas the negative control antibody did not inhibit proliferation. Moreover, a similar inhibition is observed in the presence of a saturating amount of BAFF, with an IC50 for bispecific antibody of 1.57±0.45 nM versus 1.41±0.50 nM for the positive control antibody (average of 3 independent experiments±SEM). The bispecific antibody of the present invention effectively neutralizes IL-17 and that this neutralization is not affected by the presence of saturating amounts of BAFF.

Inhibition of BAFF-Induced Proliferation In Vitro of T1165 Cells

T1165.17 is a murine plasmacytoma cell line that is dependent on external factors (IL-1beta or BAFF) for survival and growth. These cells naturally express the receptor for BAFF and their response to human BAFF is measured by monitoring proliferation.

A dose range of the bispecific antibody from 1 nM to 4.1 pM (final concentration based on monomeric MW of bispecific antibody (=100 kDa)) is evaluated for the ability to neutralize soluble BAFF (final soluble BAFF concentration in assay is 150 pM based on monomeric MW of BAFF (=20 kDa)). Various concentrations of bispecific antibody are incubated with soluble BAFF for 30-60 minutes at 37° C. in the inner wells of a flat bottom 96 well tissue culture plate in a total volume of 50 mcl. A BAFF neutralizing antibody (4A5-3.1.1-B4 of U.S. Pat. No. 7,317,089) is used as positive control in the assay. Each condition is tested in triplicate. In a variation of this assay, the ability of bispecific antibody to neutralize membrane BAFF is tested. Various concentrations of bispecific antibody are incubated with the membrane fraction of HEK293 cells expressing a non-cleavable form of BAFF (achieved by mutating the furin cleavage site in BAFF, resulting in permanent expression of BAFF on the cell membrane). In another variation of this assay, a saturating concentration of human IL-17 is added (15.6 nM final concentration, based on monomeric MW of IL-17 (=16 kDa)), with the goal to determine if bispecific antibody would still be able to neutralize either soluble or membrane BAFF when simultaneously bound to IL-17.

T1165 cells are routinely cultured in assay medium (RPMI1640 containing 10% FBS, HEPES, L-Glutamine, 1 mM Sodium Pyruvate, $5 \times 10^{-5}$M 2-mercaptoethanol, 1× Antibiotic-Antimycotic) supplemented with 2 ng/mL recombinant human IL-1beta. On the day of the assay cells are washed 3 times with assay medium and resuspended to $1 \times 10^5$ cells/mL in assay medium. Fifty mcl of the cell suspension is added to the 96 well plate, containing the mixture of antibody and BAFF. One hundred mcl of assay medium is added to each of the unused edge wells (without cells) to reduce edge effects resulting from evaporation. Plates are placed in a tissue culture incubator (37° C., 95% relative humidity, 5% CO2) for approximately 44 hours. At the end of the assay 20 mcl of Promega Cell Titer 96 Aqueous One Solution is added to each well and incubated for 1 to 4 hours at 37° C. Plates are read at 490 nm on a microplate reader (Molecular Devices SpectraMax 190). Data are collected as % inhibition, using wells without BAFF as the minimum and wells with 150 pM BAFF as the maximum responses. The concentration where 50% of the BAFF-induced response is inhibited (IC50) by either bispecific antibody or the positive control is calculated using a 4 parameter sigmoidal fit of the data (SigmaPlot).

The results demonstrate that the bispecific antibody inhibits soluble BAFF-induced proliferation of T1165 cells in a concentration-dependent manner. This inhibition is comparable to that observed with the positive control antibody (with an IC50 for bispecific antibody of 0.064±0.021 pM versus 0.071±0.002 pM for the positive control antibody (average of 2 independent experiments±SEM)), whereas the negative control antibody did not inhibit proliferation. Moreover, a similar inhibition is observed in the presence of a saturating amount of IL-17, with an IC50 for bispecific antibody of 0.060±0.014 pM versus 0.073±0.012 pM for the positive control antibody (average of 2 independent experiments±SEM). The bispecific antibody effectively neutralizes BAFF and this neutralization is not affected by the presence of saturating amounts of IL-17.

The ability of bispecific antibody to inhibit proliferation of T165 cells induced by membrane-bound BAFF is also demonstrated. The bispecific antibody of the present invention effectively inhibits proliferation induced by membrane-bound BAFF similarly to the positive control BAFF antibody (4A5-3.1.1-B4 of U.S. Pat. No. 7,317,089). Moreover, similar inhibition is observed in the presence of a saturating amount of IL-17.

Inhibition of Human IL-17-Induced Production of CXCL1 In Vivo

Injection of human IL-17 leads to a rapid and transient increase in mouse CXCL1 in the circulation. Regular female C57B16 mice (n=8 per group) are injected SC with either bispecific antibody (66 mcg/mouse), or a positive control anti-IL-17 antibody (Fab 126 of U.S. Pat. No. 7,838,638, 50 mcg/mouse) or negative control antibody (huIgG4, 50 mcg/mouse). Two days later, mice receive a single IP injection of human IL-17 (3 mcg/mouse) and 2 hours later serum is collected and stored at −80° C. until analysis. The concentration of CXCL1 is determined by ELISA. Microtiter plates are coated with an antibody capturing human Fc (Jackson ImmunoResearch 109-005-098, 1 mcg/mL) and incubated overnight at 4° C. Plates are washed, blocked with casein, and 100 mcl of serum (1:1000 dilution) is added. Plates are incubated for 2 h at RT, washed and an HRP-labeled detection antibody (anti-human IgG, Jackson ImmunoResearch 709-035-149) is added. Plates are incubated for 1 h at RT, washed and developed using TMB substrate and read using a plate reader. The concentration is calculated based on appropriate standard curves.

TABLE 3

IL-17-induced levels of CXCL1 after exposure to bispecific antibody.

| Ab dosed | Neg control | Neg control | Pos control | Bispecific antibody |
|---|---|---|---|---|
| Ligand | PBS | IL-17 | IL-17 | IL-17 |
| MEAN pg CXCL1/mL | 45.06 | 1071.17 | 482.73 | 387 |
| SEM | 45.06 | 141.67 | 263.7 | 175.11 |
| p value | | | <0.01 | <0.01 |

These data confirms that human IL-17 results in an increase in serum CXCL1 levels. However, in the presence of the bispecific antibody these results demonstrate that the IL-17-induced increase of CXCL1 is reduced (P<0.01, ANOVA) relative to animals that receive the negative control antibody. The reduction in CXCL1 with bispecific antibody is comparable to that observed with the positive control anti-IL-17 antibody. Equivalent exposure to either bispecific antibody, the positive and negative control antibodies within each group is confirmed by quantitative ELISA. Thus, bispecific antibody of the present invention effectively neutralizes biological effects induced by human IL-17 in the mouse. P value determination is compared to negative control/IL-17 group.

Inhibition of Human BAFF In Vivo

Mice that carry a transgene encoding soluble human BAFF have an abnormally high number of B lymphocytes in the spleen.

Mice transgenic for human BAFF (n=5 per group) are injected IP with either a single dose of bispecific antibody (660 mcg/mouse), or a positive control anti-BAFF antibody (4A5-3.1.1-B4 U.S. Pat. No. 7,317,089, 500 mcg/mouse) or negative control antibody (huIgG4, 500 mcg/mouse). Eight days later, serum and spleens are collected. A single cell suspension of spleen cells is prepared and the total number of leukocytes is determined after lysing the red blood cells. The relative percentage of B lymphocytes is determined using the cell surface marker B220 by flow cytometry. The total number of B cells per spleen is calculated by multiplying the percentage of B220 positive cells by the total number of lymphocytes in the spleen. Microtiter plates are coated with an antibody capturing human Fc (Jackson ImmunoResearch 109-005-098, 1 mcg/mL) and incubated overnight at 4° C. Plates are washed, blocked with casein, and 100 mcl of serum (1:5000 dilution) is added. Plates are incubated for 2 h at RT, washed and an HRP-labeled detection antibody (anti-human IgG, Jackson ImmunoResearch 709-035-149) is added. Plates are incubated for 1 h at RT, washed and developed using TMB substrate and read using a plate reader. The concentration is calculated based on appropriate standard curves.

TABLE 4

B cell numbers in the spleen of mice transgenic for human BAFF after exposure of bispecific antibody.

| Ab dosed | Neg control | Pos control | Bispecific antibody |
|---|---|---|---|
| MEAN number × 10E6 B cells/spleen | 234.84 | 78.87 | 94.77 |
| SEM | 18.93 | 3.49 | 2.34 |
| p value | | <0.0001 | <0.0001 |

These results demonstrate that the number of B cells in the spleens of mice transgenic for human BAFF is reduced (p<0.0001, ANOVA) by a single administration of bispecific antibody. This normalization of B cell numbers is equivalent to that observed with the positive control BAFF antibody. Equivalent exposure to either bispecific antibody, the positive and negative control antibodies within each group is confirmed by quantitative ELISA. Thus, bispecific antibody of the present invention effectively neutralizes biological effects induced by human BAFF in the mouse. P value determination is compared to negative control group.

Solubility and Stability Analysis

The bispecific antibody is formulated in PBS at pH 7.4. The bispecific antibody is concentrated from 1-2 mg/mL to a concentration ranging from 52 mg/mL to 58 mg/mL using Amicon concentrators. Concentrated samples are stored at 25° C. over a period of 4 weeks. Samples are analyzed for percent high molecular weight (% HMW) with size exclusion chromatography (SEC) at initial concentration, 1 day, 1 week, and 4 weeks incubations. SEC is performed on a Agilent 1100 system using a TSK G3000SW-XL (Tosoh Bioscience) column. PBS+0.35M NaCl, pH 7.4 is used as the mobile phase running at 0.5 ml/min for 35 minutes. A volume of 1 uL of the concentrated antibody is injected into the column and the detection is measured at 280 nm. Chromatograms are analyzed using ChemStation and % high molecular weight (HMW) is calculated using the ratio of AUC of the peaks eluted before the monomer peak to total AUC. Samples stored at 25° C. at different time points are analyzed for % HMW and the results are summarized in Table 5.

TABLE 5

Summary of % high molecular weight species measured by SE-HPLC.

| | % HMW by SE-HPLC |
|---|---|
| Initial, unconcentrated | 0.95 |
| Initial, concentrated | 1.63 |
| 1 day 25° C. | 1.81 |
| 1 week 25° C. | 2.61 |
| 4 week 25° C. | 5.35 |

Preliminary studies with a starting bispecific antibody comprising a BAFF antibody of WO2003016468 and an IL-17 antibody of WO2007070750 demonstrated that after concentration to only 6 mg/mL, a 25% increase in % HMW species was detected by SE-HPLC after 3 weeks storage at 4° C. in PBS, and at 30 mg/mL the increase in % HMW species was 15% after just 2 days storage at 4° C. in PBS. These results demonstrate that the bispecific antibody of the present invention has much improved properties, including decreased aggregation and increased physical stability, over the starting bispecific antibody.

---

We claim:

1. An anti-BAFF-anti-IL-17 bispecific antibody comprising a first polypeptide and a second polypeptide, wherein the first polypeptide comprises HCVR1, a heavy chain constant region (CH), a first linker (L1), HCVR2, a second linker (L2), and LCVR2, wherein the HCVR1, CH, L1, HCVR2, L2, and LCVR2 are arranged from amino-terminus to carboxyl-terminus in the following order: HCVR1, CH, L1, HCVR2, L2, and LCVR2, and wherein the second polypeptide comprises LCVR1 and a light chain constant region (CL), wherein the LCVR1 is at the amino-terminus and the CL is at the carboxyl-terminus, and wherein HCVR1 comprises amino acids 1-123 of SEQ ID NO:1, HCVR2 comprises amino acids 464-582 of SEQ ID NO:1, LCVR2 comprises amino acids 603-714 of SEQ ID NO:1, and LCVR1 comprises amino acids 1-107 of SEQ ID NO:2.

2. An anti-BAFF-anti-IL-17 bispecific antibody comprising a first polypeptide and a second polypeptide, wherein the first polypeptide comprises HCVR1, a heavy chain constant region (CH), a first linker (L1), HCVR2, a second linker (L2), and LCVR2, wherein the HCVR1, CH, L1, HCVR2, L2, and LCVR2 are arranged from amino-terminus to carboxyl-terminus in the following order: HCVR1, CH, L1, HCVR2, L2, and LCVR2, and wherein the second polypeptide comprises LCVR1 and a light chain constant region (CL), wherein the LCVR1 is at the amino-terminus and the CL is at the carboxyl-terminus, and wherein HCVR1 comprises CDRH1-1, CDRH1-2, and CDRH1-3, and HCVR2; comprises CDRH2-1, CDRH2-2, and CDRH2-3, and LCVR2 comprises CDRL2-1, CDRL2-2, and CDRL2-3, and LCVR1 comprises CDRL1-1, CDRL1-2, CDRL1-3, and wherein:

CDRH1-1 comprises amino acids 27-35 of SEQ ID NO:1;
CDRH1-2 comprises amino acids 50-65 of SEQ ID NO:1;
CDRH1-3 comprises amino acids 98-112 of SEQ ID NO:1;
CDRH2-1 comprises amino acids 488-498 of SEQ ID NO:1;
CDRH2-2 comprises amino acids 513-528 of SEQ ID NO:1;
CDRH2-3 comprises amino acids 562-571 of SEQ ID NO:1;
CDRL2-1 comprises amino acids 626-641 of SEQ ID NO:1;
CDRL2-2 comprises amino acids 657-663 of SEQ ID NO:1;
CDRL2-3 comprises amino acids 696-704 of SEQ ID NO:1;
CDRL1-1 comprises amino acids 24-34 of SEQ ID NO:2;
CDRL1-2 comprises amino acids 50-56 of SEQ ID NO:2; and
CDRL1-3 comprises amino acids 89-97 of SEQ ID NO:2.

3. A method of treating Systemic Lupus Erythematosus, Lupus Nephritis, Rheumatoid Arthritis, Psoriasis, Ankylosing Spondylitis, Psoriatic Arthritis, primary Sjögren's syndrome, or Multiple Myeloma comprising administering to a patient in need thereof an effective amount of the bispecific antibody of claim 1.

4. A method of treating Systemic Lupus Erythematosus, Lupus Nephritis, Rheumatoid Arthritis, Psoriasis, Ankylosing Spondylitis, Psoriatic Arthritis, primary Sjögren's syndrome, or Multiple Myeloma comprising administering to a patient in need thereof an effective amount of the bispecific antibody of claim 2.

5. A pharmaceutical composition comprising the bispecific antibody of claim 1 and one or more pharmaceutically acceptable carriers, diluents or excipients.

6. A pharmaceutical composition comprising the bispecific antibody of claim 2 and one or more pharmaceutically acceptable carriers, diluents or excipients.

* * * * *

UNITED STATES PATENT AND TRADEMARK OFFICE
CERTIFICATE OF CORRECTION

PATENT NO. : 9,708,402 B2
APPLICATION NO. : 15/157782
DATED : July 18, 2017
INVENTOR(S) : Barrett Allan It is certified that error appears in the above-identified patent and that said Letters Patent is hereby corrected as shown below:

Column 25, Line 62 In Claim 2, delete "HCVR2;" and insert -- HCVR2 --, therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*